United States Patent
Ehmke

(10) Patent No.: US 10,610,368 B2
(45) Date of Patent: Apr. 7, 2020

(54) ANKLE FUSION SYSTEM WITH EXPANDABLE SPACER

(71) Applicant: Acumed LLC, Hillsboro, OR (US)

(72) Inventor: Larry W. Ehmke, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 27 days.

(21) Appl. No.: 15/990,633

(22) Filed: May 26, 2018

(65) Prior Publication Data
US 2019/0358046 A1 Nov. 28, 2019

(51) Int. Cl.
*A61F 2/42* (2006.01)
*A61F 2/46* (2006.01)
*A61F 2/30* (2006.01)
*A61B 17/16* (2006.01)

(52) U.S. Cl.
CPC ........ *A61F 2/4202* (2013.01); *A61B 17/1682* (2013.01); *A61F 2/30749* (2013.01); *A61F 2/4606* (2013.01); *A61F 2002/3055* (2013.01); *A61F 2002/3069* (2013.01); *A61F 2002/30245* (2013.01); *A61F 2002/30405* (2013.01); *A61F 2002/30579* (2013.01); *A61F 2002/30622* (2013.01); *A61F 2002/30754* (2013.01); *A61F 2002/30841* (2013.01); *A61F 2002/30884* (2013.01); *A61F 2002/4205* (2013.01); *A61F 2002/4207* (2013.01)

(58) Field of Classification Search
CPC .. A61F 2/28; A61F 2/30; A61F 2/4202; A61F 2/4606; A61B 17/1682
See application file for complete search history.

(56) References Cited

U.S. PATENT DOCUMENTS

| | | | |
|---|---|---|---|
| 4,467,794 A | 8/1984 | Maffei et al. |
| 4,938,768 A | 7/1990 | Wu |
| 5,211,664 A | 5/1993 | Tepic et al. |
| 6,572,620 B1 | 6/2003 | Schon et al. |
| 6,579,293 B1 | 6/2003 | Chandran |

(Continued)

FOREIGN PATENT DOCUMENTS

| | | |
|---|---|---|
| EP | 3030198 A1 | 6/2016 |
| EP | 1848355 B1 | 1/2018 |

(Continued)

OTHER PUBLICATIONS

Additive Orthopedics, Tibial Cage picture, Feb. 5, 2018, 1 pg.
(Continued)

*Primary Examiner* — Jason-Dennis N Stewart
(74) *Attorney, Agent, or Firm* — Kolisch Hartwell, P.C.

(57) ABSTRACT

System, including apparatus and methods, for ankle fusion using a device for separating a first bone and a second bone of an ankle region. In some embodiments, the device may comprise an expandable spacer including first and second bone-contacting surface regions facing away from one another and configured to be abutted with the first and second bones, respectively. A distance between the first and second bone-contacting surface regions may be adjustable to change the separation of the first and second bones. The first bone-contacting surface region may correspond to a portion of a sphere and may be configured to be disposed at least partially in a concavity formed surgically in the first bone. The expandable spacer offers improved control over the length of the lower limb and the orientation of the foot during ankle fusion surgery.

22 Claims, 13 Drawing Sheets

(56) References Cited

U.S. PATENT DOCUMENTS

| | | |
|---|---|---|
| 7,544,208 B1 | 6/2009 | Mueller et al. |
| 7,575,601 B2 | 8/2009 | Dickson |
| 7,608,075 B2 | 10/2009 | Tornier |
| 7,717,920 B2 | 5/2010 | Reiley |
| 7,963,996 B2 | 6/2011 | Saltzman et al. |
| 8,057,520 B2 | 11/2011 | Ducharme et al. |
| 8,114,091 B2 | 2/2012 | Ratron et al. |
| 8,152,852 B2 | 4/2012 | Biyani |
| 8,187,308 B2 | 5/2012 | Mullaney et al. |
| 8,231,662 B2 | 7/2012 | Huebner |
| 8,328,807 B2 | 12/2012 | Brigido |
| 8,328,809 B2 | 12/2012 | Wenk et al. |
| 8,353,963 B2 | 1/2013 | Glerum |
| 8,579,899 B2 | 11/2013 | Ahmadi |
| 8,585,744 B2 | 11/2013 | Duggal et al. |
| 8,632,593 B2 | 1/2014 | Suh et al. |
| 8,657,820 B2 | 2/2014 | Kubiak et al. |
| 8,715,363 B2 | 5/2014 | Ratron et al. |
| 8,808,334 B2 | 8/2014 | Strnad et al. |
| 8,974,538 B2 | 3/2015 | Teeny et al. |
| 9,155,553 B2 | 10/2015 | Zipnick |
| 9,220,518 B2 | 12/2015 | Neal et al. |
| 9,308,037 B2 | 4/2016 | Richter et al. |
| 9,326,861 B2 | 5/2016 | Iott et al. |
| 9,480,511 B2 | 11/2016 | Butters et al. |
| 9,492,178 B2 | 11/2016 | Neal et al. |
| 9,962,201 B2 | 5/2018 | Duggal et al. |
| 2004/0039394 A1 | 2/2004 | Conti et al. |
| 2005/0107791 A1 | 5/2005 | Manderson |
| 2007/0123857 A1 | 5/2007 | Deffenbaugh et al. |
| 2007/0276401 A1 | 11/2007 | Choe et al. |
| 2009/0143825 A1 | 6/2009 | Graham et al. |
| 2009/0157086 A1 | 6/2009 | Digeser et al. |
| 2009/0164017 A1 | 6/2009 | Sommerich et al. |
| 2009/0248084 A1 | 10/2009 | Hintermann |
| 2010/0114315 A1 | 5/2010 | Manderson |
| 2010/0262150 A1 | 10/2010 | Lian |
| 2012/0245701 A1 | 9/2012 | Zak et al. |
| 2013/0172942 A1 | 7/2013 | Lewis et al. |
| 2014/0018931 A1 | 1/2014 | Gillard et al. |
| 2014/0058524 A1 | 2/2014 | Gray |
| 2014/0066996 A1 | 3/2014 | Price et al. |
| 2014/0107798 A1 | 4/2014 | Jeng et al. |
| 2014/0163683 A1 | 6/2014 | Seifert et al. |
| 2014/0277532 A1 | 9/2014 | Teeny et al. |
| 2015/0157340 A1 | 6/2015 | McGinley et al. |
| 2016/0135815 A1 | 5/2016 | Loring et al. |
| 2016/0235548 A1 | 8/2016 | McLaughlin et al. |
| 2016/0338842 A1 | 11/2016 | Adams |
| 2016/0367377 A1 | 12/2016 | Faulhaber |
| 2018/0085151 A1 | 3/2018 | Abdelgawad |

FOREIGN PATENT DOCUMENTS

| | | |
|---|---|---|
| EP | 2756814 B1 | 3/2018 |
| FR | 2924593 A1 | 6/2009 |
| GB | 2401794 B | 12/2005 |
| JP | 2011515172 A | 5/2011 |
| WO | 2006091807 A2 | 8/2006 |
| WO | 2007131287 A1 | 11/2007 |
| WO | 2014127303 A1 | 8/2014 |

OTHER PUBLICATIONS

Cuttica, Daniel J., "Femoral Head Allograft for Tibiotalocalcaneal Fusion Using a Cup and Cone Reamer Technique", The Journal of Foot & Ankle Surgery 50 (2011), pp. 126-129.

Kreulen, Christopher et al., "Technique for Use of Trabecular Metal Spacers in Tibiotalocalcaneal Arthrodesis with Large Bony Defects", Surgical Strategies, American Orthopaedic Foot & Ankle Society, 2016, pp. 1-11.

Louisville Orthopaedic Clinic, "Use of Large Allografts for Hindfoot and Ankle Fusion" web pages, (c) 2019, 5 pgs.

Musculoskeletal Key, "Femoral Head Allograft for Large Talar Defects Using a Lateral Approach", web pages, May 27, 2017, 4 pgs.

Myers, Stuart H. et al., "The Zimmer Trabecular Metal Total Ankle System: Features and Techniques", Total Ankle Replacement: An Operative Manual, Ch. 8, (c) 2013, pp. 67-78.

Young, Lee W., Authorized Officer, ISA/US, Commissioner for Patents, "International Search Report" and "Written Opinion of the International Searching Authority" in connection with related International Application No. PCT/US2019/033818, dated Aug. 15, 2019, 7 pgs.

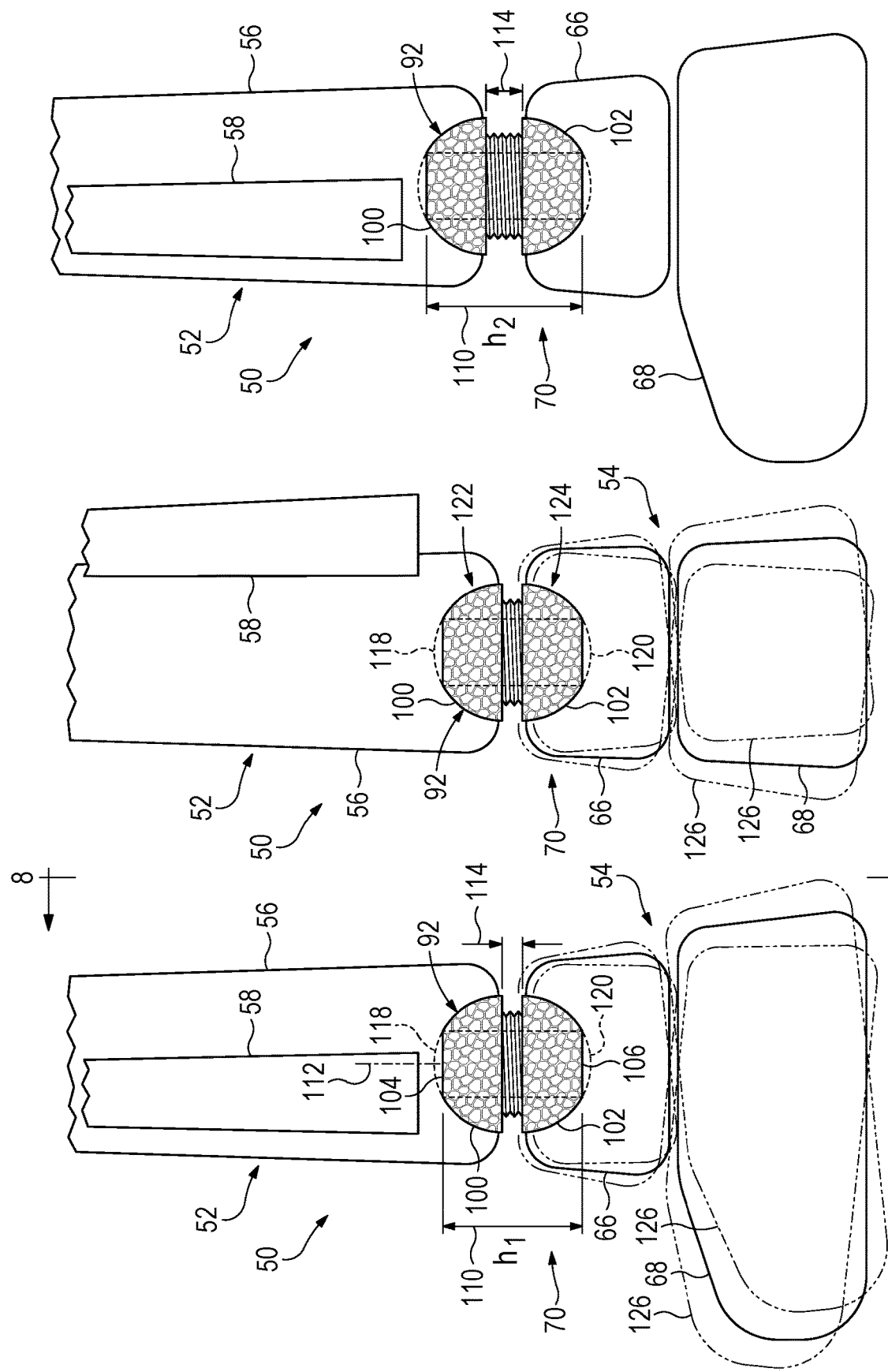

ANKLE FUSION SYSTEM WITH EXPANDABLE SPACER

INTRODUCTION

The human skeleton is composed of 206 individual bones connected to one another by joints. Each joint determines the relative mobility of two or more adjacent bones. For example, synovial joints are found between bones having the greatest freedom of motion and enable bones of the appendages to move relative to one another and the axial skeleton.

Synovial joints can become damaged with age, overuse, or traumatic injury, among others, often resulting in chronic pain. A damaged joint may be treated surgically by partial or total arthroplasty (joint replacement) or by arthrodesis, which fuses bones to one another.

FIG. 1 shows a distal, skeletal portion of a human lower limb 50, including the bones of lower leg 52 and foot 54. The skeletal portion of lower leg 52 is formed by the tibia 56 medially and the fibula 58 laterally. Skeletal foot 54 is connected to the distal ends of tibia 56 and fibula 58, and is composed of the tarsus 60 (the seven bones of the hindfoot and midfoot), the metatarsus 62 (the five bones located between the midfoot and the toes), and the phalanges 64 (the bones of the toes). The skeletal hindfoot is formed by only two bones, the talus 66 (the ankle bone) and the calcaneus 68 (the heel bone), which are stacked under lower leg 52.

Lower limb 50 forms an ankle region 70 where lower leg 52 and foot 54 meet one another. Ankle region 70 includes three joints at which four bones articulate with one another. The talocrural joint 72 (the "true ankle joint") is a synovial hinge joint connecting tibia 56 and fibula 58 distally to the proximal end of talus 66. Dorsiflexion or plantarflexion of the foot (movement in a sagittal plane) occurs when talus 66 is rolled in a mortise formed collectively by tibia 56 and fibula 58. The subtalar joint 74 is a planar synovial joint at which the distal end of talus 66 articulates at two points with calcaneus 68. Eversion and inversion of foot 54 involves movement at subtalar joint 74. The inferior tibiofibular joint 76 is formed where a lateral surface region of distal tibia 56 articulates with a medial surface region of distal fibula 58.

Damage to the talocrural joint of ankle region 70 can be treated by partial or total ankle replacement arthroplasty. In this procedure, at least one articular surface of the joint is replaced by an ankle prosthesis. However, for various reasons, such as poor bone quality, fracture, or the like, the ankle replacement may fail and removal of the ankle prosthesis may be required.

A failed ankle replacement or other large defect/gap in the ankle region is often treated by arthrodesis to fuse tibia 56 and talus 66, or tibia 56 and calcaneus 68, to one another. Fusion may be promoted surgically by ablation of cartilage between bones and/or removal of some subchondral bone, followed by bone fixation to produce bony union over time. Fixation can be achieved by securing a fixation device(s), such as a nail, plate, screw, or a combination thereof, among others, to each of the bones to be fused.

FIGS. 2-4 illustrate various prior art configurations for ankle fusion. FIG. 2 shows tibia 56 and talus 66 firmly attached to one another using a bone plate 78. Bone screws 80 secure bone plate 78 on the posterior side of tibia 56 and talus 66. Fibula 58 may be full-length, as shown here, or may be truncated. FIG. 3 shows bone screws 80 firmly attaching tibia 56, fibula 58, and talus 66 to one another. A pair of bone screws 80 span talocrural joint 72. A distal end of fibula 58 has been resected, indicated at 82, and a bone screw 80 secures shortened fibula 58 to tibia 56 by spanning tibiofibular joint 76. FIG. 4 shows an intramedullary nail 84 and associated bone screws 80 firmly attaching tibia 56, talus 66, and calcaneus 68 to one another in a tibiotalocalcaneal (TTC) fusion. To achieve fixation, the leading end of nail 84 can be inserted in a retrograde direction, from a plantar surface of the foot, through calcaneus 68 and talus 66, and into tibia 56, and then nail 84 can be secured with screws 80. Fibula 58 may be resected, as shown, and secured to tibia 56 using one or more bone screws 80 that extend through nail 84 and from tibia 56 to fibula 58.

Spanning a large gap/defect in the ankle region to restore proper limb length and the ability to bear weight presents a real challenge to the clinician; fixation devices alone are inadequate. Accordingly, a bone graft may be placed between the bones to fill empty space, encourage bone growth and remodeling, and help to stabilize the position of the bones. For example, femoral head allografts have been used in ankle arthrodesis to fill the gap between bones to be fused. However, these allografts have a fixed axial dimension, which makes restoring limb length problematic. Other complications associated with femoral head allografts include latent infection, decreased mechanical strength following sterilization, and an increased risk of fracture, collapse, or nonunion. An improved ankle fusion system is needed.

SUMMARY

The present disclosure provides a system, including apparatus and methods, for ankle fusion using a device for separating a first bone and a second bone of an ankle region. In some embodiments, the device may comprise an expandable spacer including first and second bone-contacting surface regions facing away from one another and configured to be abutted with the first and second bones, respectively. A distance between the first and second bone-contacting surface regions may be adjustable to change the separation of the first and second bones. The first bone-contacting surface region may correspond to a portion of a sphere and may be configured to be disposed at least partially in a concavity formed surgically in the first bone. The expandable spacer offers improved control over the length of the lower limb and the orientation of the foot during ankle fusion surgery.

BRIEF DESCRIPTION OF THE DRAWINGS

FIG. 7 is a schematic, fragmentary, lateral view of only the ankle region bones of the right lower limb of a human skeleton, taken during installation of the ankle fusion system of FIG. 5 but with only the spacer present, and illustrating, in phantom outline, exemplary adjustment of the orientation of the talus and calcaneus relative to the tibia in a sagittal plane.

FIG. 8 is a posterior view of the ankle region bones and spacer of FIG. 7, illustrating, in phantom outline, exemplary adjustment of the orientation of the talus and calcaneus relative to the tibia generally in a frontal plane.

FIG. 9 is another lateral view of the ankle region bones and spacer of FIG. 7, taken after exemplary adjustment of the height of the spacer to change the separation between the tibia and talus of the ankle region before they are fixed relative to one another.

DETAILED DESCRIPTION

Figures 1, 2:
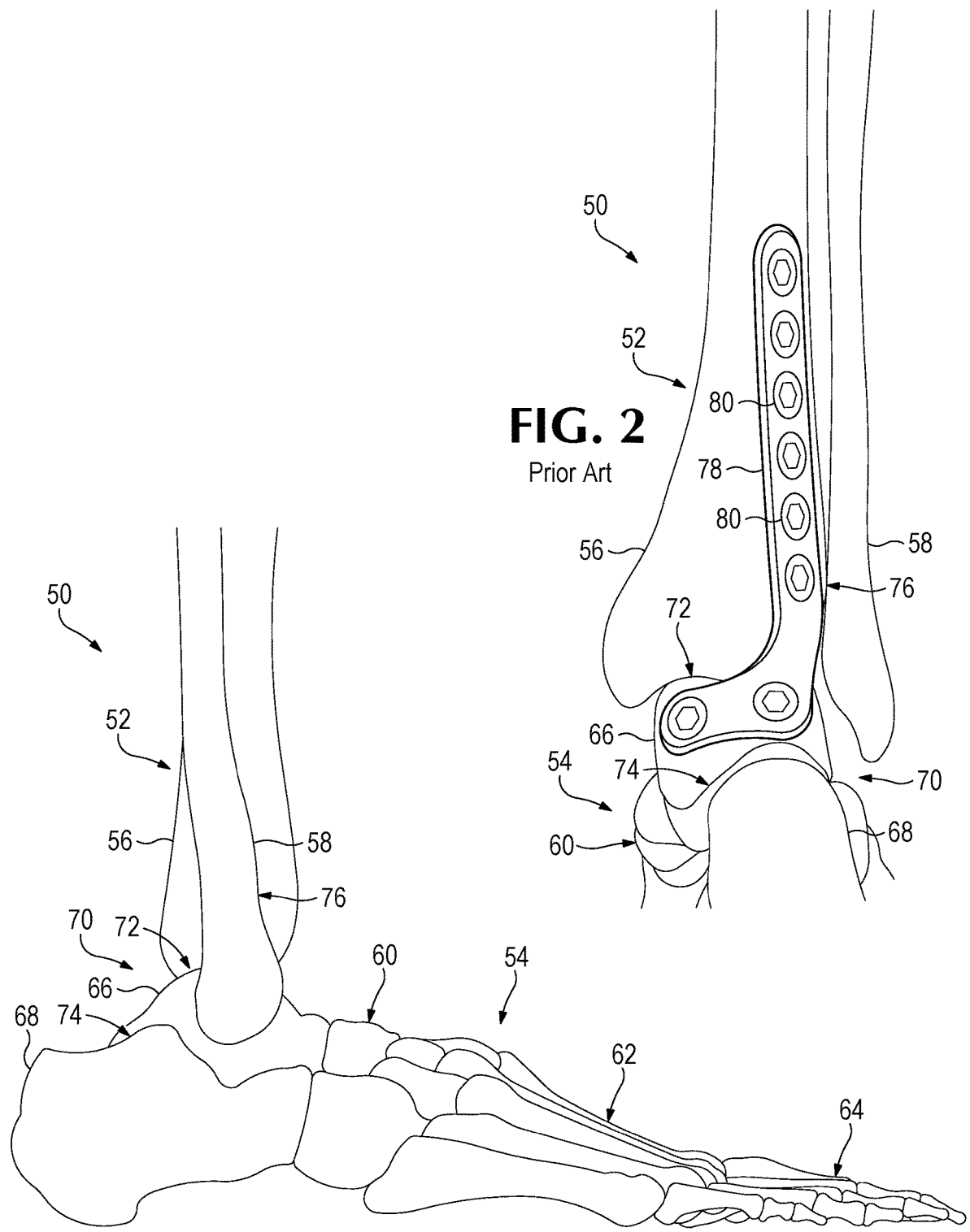
FIG. 1 is a lateral view of the distal portion of the right lower limb of a human skeleton, with the bones of the lower leg depicted as fragmentary.
FIG. 2 is a fragmentary, posterior view of the right lower limb of FIG. 1, taken after securing a bone plate to the tibia of the lower leg, and to the talus of the foot, using bone screws, to illustrate a prior art configuration for fusion of the tibia and talus of the ankle region to one another.

The present disclosure provides a system, including apparatus and methods, for ankle fusion using a device for separating a first bone and a second bone of an ankle region. In some embodiments, the device may comprise an expandable spacer including first and second bone-contacting surface regions facing away from one another and configured to be engaged with the first and second bones, respectively. A distance between the first and second bone-contacting surface regions may be adjustable to change the separation of the first and second bones. The first bone-contacting surface region may correspond to a portion of a sphere and may be configured to be disposed at least partially in a concavity formed surgically in the first bone. The expandable spacer offers improved control over the length of the lower limb and the orientation of the foot during ankle fusion surgery.

The spacer may have any suitable combination of features. The bone-contacting surface regions both may be spherical, or one may be spherical and the other planar, among others. One or both bone-contacting surface regions, and/or other regions of the spacer, may be configured to encourage bone on-growth and/or bone in-growth, to promote efficient osseointegration of the spacer after implantation. The distance between the bone-contacting surface regions may be adjusted with a height-adjustment mechanism, which may include a threaded mechanism, a rack-and-pinion mechanism, an axially slidable mechanism (e.g., a ratchet mechanism), or the like. The height-adjustment mechanism may be self-locking or may be locked at a selected height of the spacer with a locking member (e.g., a set screw). In some embodiments, the height-adjustment mechanism may include an internally-threaded collar that is rotatable in opposite directions with respect to the bone-contacting surface regions to either increase or decrease the distance between such surface regions.

The ankle fusion system may comprise the expandable spacer, at least one fixation device to fix at least the first and second bones relative to one another, one or more fasteners to attach the fixation device to bone and/or to the spacer, at least one (non-implanted) tool to drive adjustment of the distance between the bone-contacting surface regions of the spacer and/or to manipulate a locking member such that the spacer is locked at this distance, a reamer to create the concavity in the first bone (and optionally another concavity in the second bone) during ankle fusion surgery, a saw or other cutting tool (e.g., a milling tool) to create a flat surface region on the second bone (if the second bone-contacting surface region is planar), a guide device defining a guide axis coaxial with a bore of the spacer, or any combination thereof, among others. The at least one fixation device may include a nail, a plate, screws, and/or the like, and may be inserted into at least one bone or placed on a surface of at least one bone. Accordingly, the at least one fixation device may span a joint or gap between the first and second bones (e.g., the tibia and talus or the tibia and calcaneus), and optionally may span another joint or gap between the second bone and a third bone of the ankle region (e.g., the talus and calcaneus). The fixation device may extend through the spacer (e.g., a nail extending axially through the spacer), may be installed at a distance from and completely outside the spacer (e.g., a plate or fasteners), or may engage the spacer (e.g., a fastener that threads into a bore of the spacer).

An exemplary method of fusing a first bone and a second bone of an ankle region is provided. In the method, a concavity may be formed in the first bone, optionally using a spherical reamer. In some embodiments, a concavity may be formed in the second bone, or a flat surface region may be formed on the second bone, among others. An expandable spacer may be disposed between the first and second bones, such that a first bone-contacting surface region of the spacer is abutted with the first bone in the concavity and such that a second bone-contacting surface region of the spacer is abutted with the second bone to produce a separation of the first bone and the second bone from one another. A distance between the first and second bone-contacting surface regions may be adjustable to change the separation of the first and second bones, and, optionally, the distance may be adjusted, such as while the spacer remains between the bones, and optionally abutted with one or both bones. The first and second bones may be fixed relative to one another, such as with any of the fixation devices described above.

Further aspects of the present disclosure are described in the following sections: (I) overview of ankle fusion systems, (II) methods of ankle fusion, and (III) examples.

I. OVERVIEW OF ANKLE FUSION SYSTEMS

This section provides an overview of the ankle fusion systems of the present disclosure, as exemplified by an ankle fusion system 90 including an expandable spacer 92 and a fixation device 94 composed of an intramedullary nail 84 and fasteners 96 (e.g., screws 80) for the nail; see FIGS. 5-12.

Figure 5:
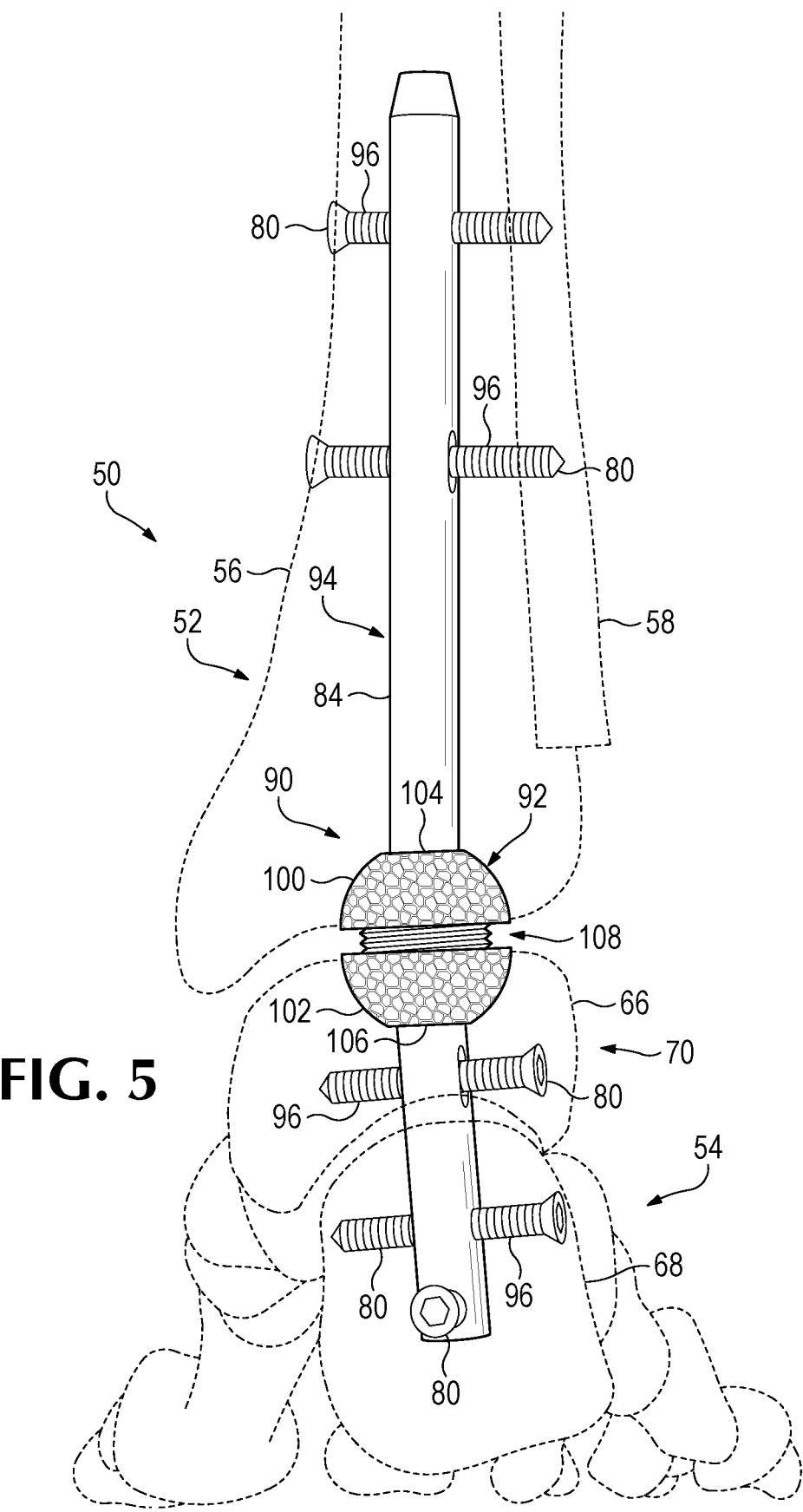
FIG. 5 is a fragmentary, posterior view of the right lower limb of a human skeleton, shown in dashed outline after installation of an exemplary ankle fusion system including an intramedullary nail and a first embodiment of an expandable (height-adjustable) spacer.
Figure 6:
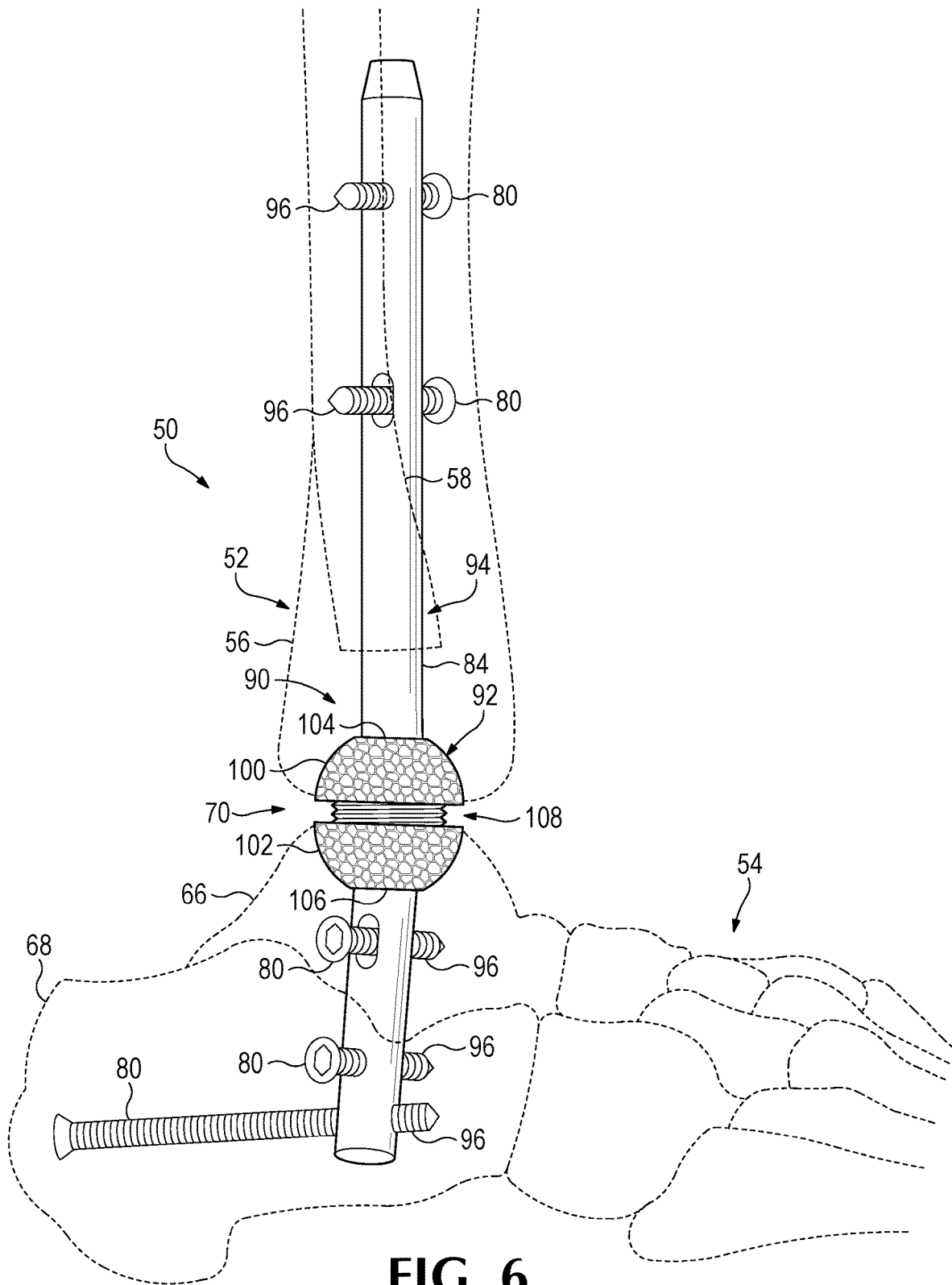
FIG. 6 is a fragmentary, lateral view of the right lower limb of FIG. 5, shown in dashed outline after installation of the ankle fusion system of FIG. 5.

FIGS. 5 and 6 show lower limb 50 after installation of system 90 for tibiotalocalcaneal fusion of tibia 56, talus 66, and calcaneus 68. Spacer 92 may set the distance between tibia 56 and talus 66, as shown, or between tibia 56 and calcaneus 68, if an intervening portion of talus 66 has been removed or is missing otherwise.

Spacer 92 has an upper section 100 and a lower section 102 configured to abut respective bones of ankle region 70. (The terms "upper" and "lower" are arbitrary and swappable with one another, unless specified otherwise, as any of the spacer embodiments disclosed herein may be installed in an inverted orientation relative to the orientation shown.) Sections 100, 102 respectively may form an upper end 104 and a lower end 106 of the spacer. A height-adjustment mechanism 108 may govern a height 110 of spacer 92 (see FIGS. 5, 7, and 9). The height may be measured between ends 104, 106 along an axis 112 of the spacer. While governing height, mechanism 108 also governs a distance 114 between sections 100, 102. Height-adjustment mechanism 108 may be configured to be adjustable in situ, that is, while sections 100, 102 remain abutted with their respective bones, and/or the height of the spacer may be adjusted prior to its implantation between bones. The height-adjustment mechanism may include a threaded connection between an external thread and an internal thread, and adjustment of the height may involve adjusting the threaded connection by threaded advancement or retraction of the threads relative to one another, and/or may include any other suitable height-adjustment mechanism and/or height-locking mechanism, as described further below.

Figure 10:
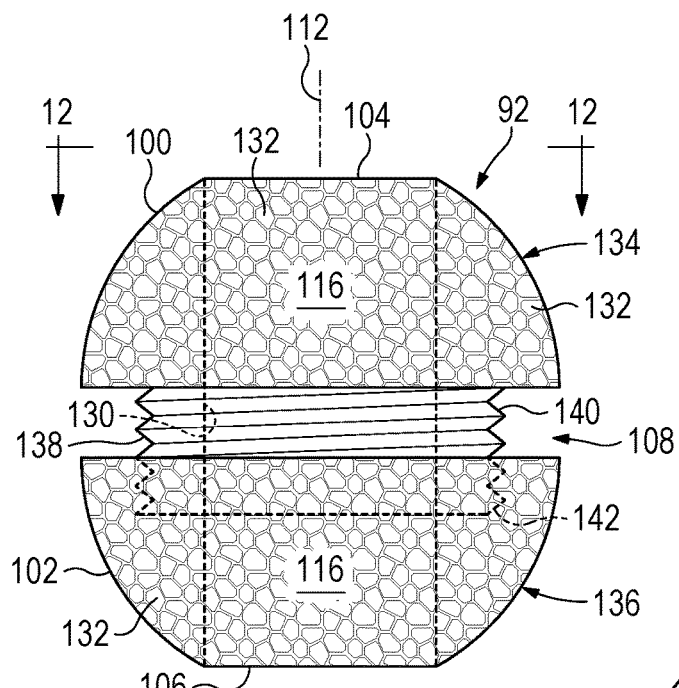
FIG. 10 is an elevational view of the spacer of FIG. 5 taken in the absence of the ankle region bones.
Figure 11:
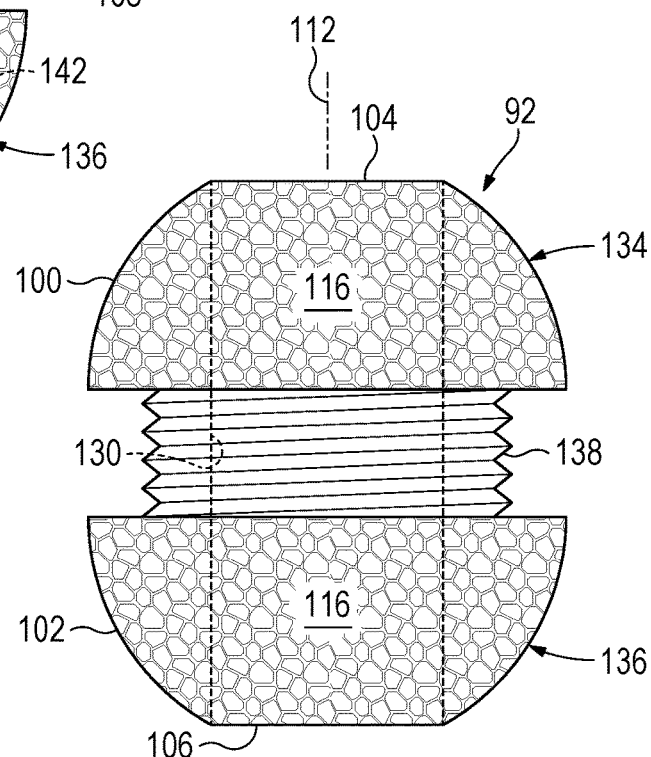
FIG. 11 is an elevational view of the spacer of FIG. 10 in a more expanded configuration.
Figure 12:
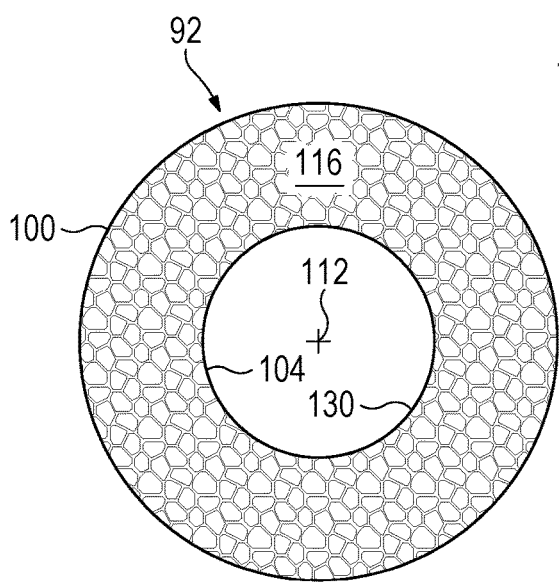
FIG. 12 is an axial view of the spacer of FIG. 10, taken generally along line 12-12 of FIG. 10.

One or both sections 100, 102 may be rounded (see FIGS. 10-12). For example, one or both sections may be rounded in a pair of orthogonal planes that intersect one another along axis 112. The diameter of the section(s), measured orthogonal to axis 112, may decrease with an arcuate taper, as the section extends toward its corresponding end 104 or 106. At least one section 100, 102 may have a bone-contacting surface region 116 that is spherical. The term "spherical," as used herein, means substantially having the form of a sphere or a segment thereof, and thus corresponding to at least a portion of a sphere. The portion may be no more than about a hemisphere and/or a frustum of a sphere. Sections 100, 102 may have the same size and/or radius of curvature, or the sizes and/or radii of curvature may be different. In some embodiments, only one of sections 100, 102 may be rounded, and the other section may be configured to be abutted with a planar surface region of a bone. This other section may have a bone-contacting surface region that is flat and optionally arranged orthogonal to axis 112, as described further below. In other embodiments, this other section may have a bone-contacting surface region with another shape, such as conical, cylindrical, or the like.

FIGS. 7-9 introduce a schematic representation of bones 56, 58, 66, and 68 to illustrate how spacer 92 permits adjustment of the relative positions of a pair of bones (tibia 56 and talus 66) of ankle region 70 before fixation. FIGS. 7 and 8 show respective lateral and posterior views of ankle region 70 after spacer 92 has been placed between bones 56, 66, with sections 100, 102 located in complementary concavities 118, 120 formed in tibia 56 and talus 66, respectively.

A spherical interface 122 formed between section 100 and tibia 56, and/or a spherical interface 124 formed between section 102 and talus 66 permits adjustment of the orientation of tibia 56 and talus 66 relative to one another (see FIG. 8). Each spherical interface corresponds to a portion of a complete sphere. The spherical interface permits adjustment of the orientation in multiple non-parallel planes, with exemplary adjustment indicated in phantom outline at 126 (see FIGS. 7 and 8). In FIG. 7, the orientation is being adjusted in a sagittal plane, to change the amount of dorsiflexion/plantarflexion of foot 54 relative to lower leg 52. In FIG. 8, the orientation is being adjusted in a frontal plane, to change the amount of eversion/inversion of foot 54 relative to lower leg 52. The orientation also or alternatively may, for example, be adjusted in a transverse plane by rotation about the long axis of the lower limb.

The height 110 of spacer 92 has been increased from $h_1$ in FIG. 7 to $h_2$ in FIG. 9, which enlarges a gap (alternatively called a separation) between tibia 56 and talus 66. This height adjustment changes the length of lower limb 50, which permits a better match with the length of the subject's other lower limb.

Figures 3, 4:
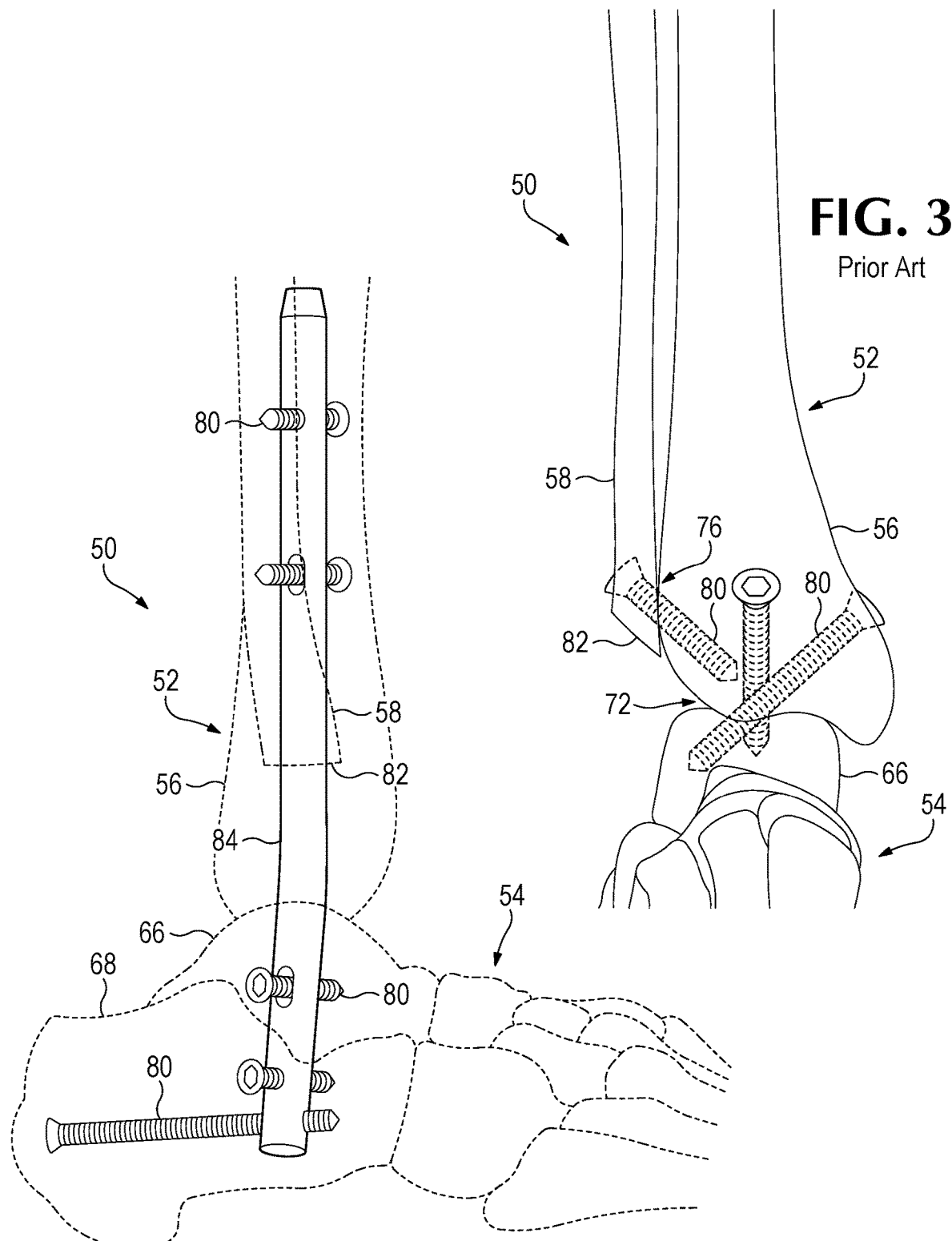
FIG. 3 is a fragmentary, anterior view of the right lower limb of FIG. 1, taken after installation of bone screws, to illustrate a prior art configuration for fusion of the tibia, the talus, and the fibula of the ankle region to one another.
FIG. 4 is a fragmentary, lateral view of the right lower limb of FIG. 1, shown in dashed outline after securing an intramedullary nail of the prior art to the tibia, talus, and calcaneus, to illustrate a prior art configuration for tibiotalocalcaneal fusion.

Nail 84 may be positioned as described above in the introduction (also see FIG. 4), but extending through spacer 92, with the nail inserted before or after the adjustment of orientation and/or height just described (see FIGS. 5 and 6). Accordingly, spacer 92 may define an axial through-opening 130 that extends through sections 100 and 102, between upper end 104 and lower end 106 coaxial with axis 112 (see FIGS. 10-12). Through-opening 130 may be oversized in diameter with respect to the nail, to permit formation of an oblique angular offset of spacer axis 112 relative to the longitudinal axis of nail 84 in the final installed configuration. The difference in diameters allows a leading portion of nail 84 to pass through spacer 92 after the orientation of the spacer has been adjusted, and/or to permit some rotation of the spacer with respect to the nail after both have been placed into bone. The nail may be secured to tibia 56, talus 66, and calcaneus 68, to fix the positions of these bones relative to one another, using fasteners, which may be bone screws 80, pegs, pins, wires, or the like, or separate fasteners may be omitted in some embodiments. In other embodiments, the nail may be replaced with a different fixation device, such as a bone plate and/or screws, and/or axial through-opening 130 may be eliminated from spacer 92 (see Section III).

FIGS. 10-12 show further aspects of spacer 92. Any suitable surface regions of spacer 92, such as bone-contacting surface regions 116 of sections 100, 102, may be configured to encourage bone on-growth and/or bone in-growth that firmly attaches the surface regions to bone. For example, each surface region may have surface features 132, such as depressions, through-holes, protrusions, and/or the like, into, through, and/or around which bone may grow. In some embodiments, the surface region may simply be roughened (e.g., by abrasion, such as grit blasting). In some embodiments, the surface region may have a plurality of pores, which may communicate with one another. In some embodiments, the surface region may have an open cellular structure, which may be created by a lattice, mesh, or foam, among others. Bone on-growth and/or bone in-growth also may be stimulated by associating a bone graft with spacer 92 on any of these surface regions and/or inside the spacer.

Spacer 92 may be composed of two, three, or more discrete components that are movable relative to one another during height adjustment. For example, the spacer may have only a first component 134 and a second component 136. First component 134 may include upper section 100 (or lower section 102) and a shaft 138 firmly attached to the section and including an external thread 140. Second component 136 may include lower section 102 (or upper section 100) and an internal thread 142 to engage external thread 140. Rotation of components 134, 136 relative to one another about axis 112 expands and contracts spacer 92. In other embodiments, shaft 138 of first component 134 (or a threaded shaft of second component 136) may be in threaded engagement with an internally threaded collar, which may be rotated to adjust the height of spacer 92 (see Section III).

The spacer may have any suitable type of height-adjustment mechanism and/or height-locking mechanism. The height-adjustment mechanism may be threaded, as discussed elsewhere herein, or non-threaded, and may be self-locking at a selected height or may require adjustment of a separate height-locking mechanism (e.g., a set screw) to lock the spacer at the height. Exemplary non-threaded height-adjustment mechanisms include a rack-and-pinion mechanism, an axially slidable interface (e.g., a ratchet mechanism and/or telescoping mechanism), interfitment structures that mate with one another at a plurality of alternative, discrete offsets, or the like. Changes to the height of the spacer may be driven with a (non-implanted) driver tool or by hand. The driver tool or the surgeon's hand(s) may be used to rotate a member of the spacer (e.g., a pinion, lead screw, threaded collar, etc.), to drive changes in the height of the spacer. The rotation may, for example, be about an axis that is parallel or orthogonal to the axis of height adjustment.

The spacers, fixation devices, and fasteners disclosed herein may have any suitable composition. Each may be formed of any suitable biocompatible material(s) and/or bioresorbable (bioabsorbable) material(s). Illustrative biocompatible materials that may be suitable include (1) metal (for example, titanium or titanium alloy, cobalt-chrome alloy, stainless steel, magnesium or magnesium alloy (e.g., an alloy including magnesium, calcium, and zinc) etc.); (2) polymer/plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) bioresorbable material or polymer/plastic (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.)); (4) ceramic; or (5) any combination thereof.

The spacer or any suitable components/portions thereof may be constructed by any suitable manufacturing techniques. For example, the spacer may be constructed by casting/molding, subtractive manufacturing (e.g., machining), and/or additive manufacturing (e.g., 3D printing). In some embodiments, the main structure of the spacer and/or bone-facing surface regions of the spacer may be formed by 3D printing, which facilitates incorporating osseointegration-promoting features into the main structure and/or bone-facing surface regions.

Further exemplary aspects of expandable spacers and their use in ankle arthrodesis are described below.

II. METHODS OF ANKLE FUSION

This section describes exemplary steps that may be performed in a method of fusing bones of an ankle region 70, with selected steps illustrated using expandable spacer 92 of FIG. 5 and a bone plate 150 as fixation device 94; see FIGS. 13-18. The steps described in this section may be performed in any suitable order and combination using any combination of the system components and features of the present disclosure.

Figure 13:
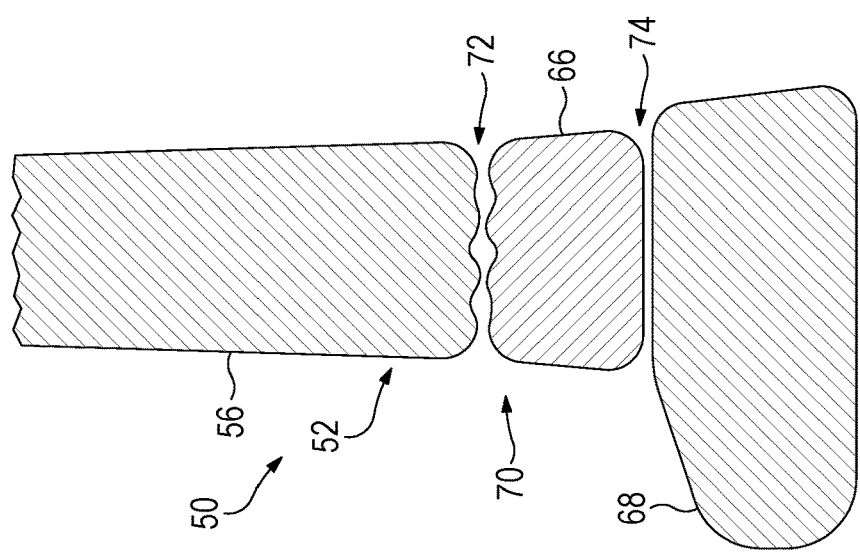

An ankle region 70 of lower limb 50 may be selected for fusion to treat any suitable indication. Exemplary indications that may be suitable include talocrural and/or subtalar arthrosis, post-traumatic arthritis of the ankle, talar avascular necrosis, failed total ankle arthroplasty, Charcot foot, complex hindfoot deformity, or severe fracture at the ankle, among others. FIG. 13 shows an ankle region 70 having arthrosis at talocrural joint 72, and can be treated by fusing tibia 56 and talus 66 to one another.

Figure 15:
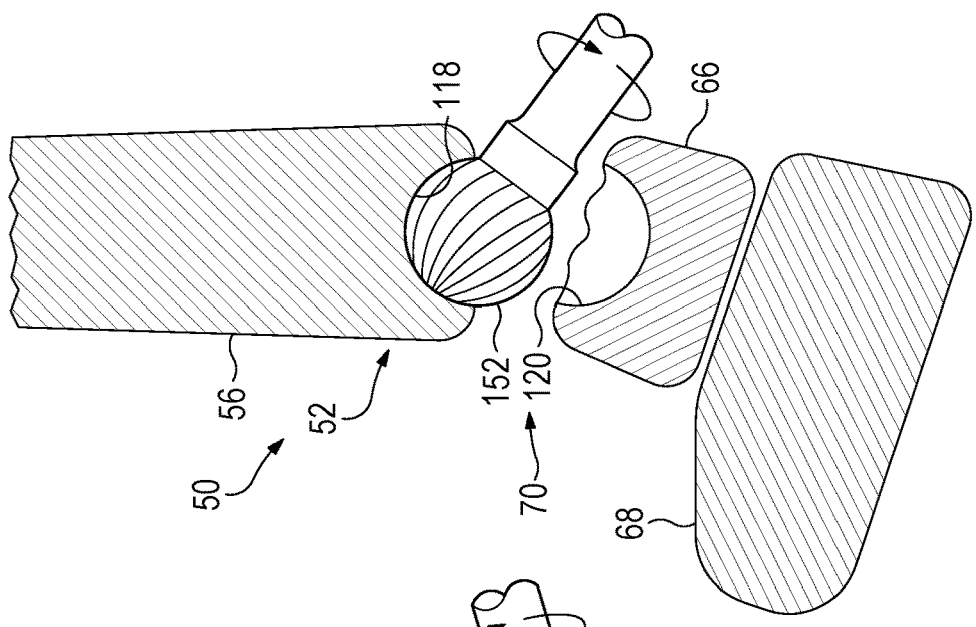
FIGS. 13 through 18 are schematic, sagittal sectional views of the tibia (shown fragmentary), talus, and calcaneus, and illustrating exemplary configurations that may be generated during performance of an exemplary method of fusing bones of an ankle region using a system including a bone plate and the spacer of FIG. 5.
Figure 14:
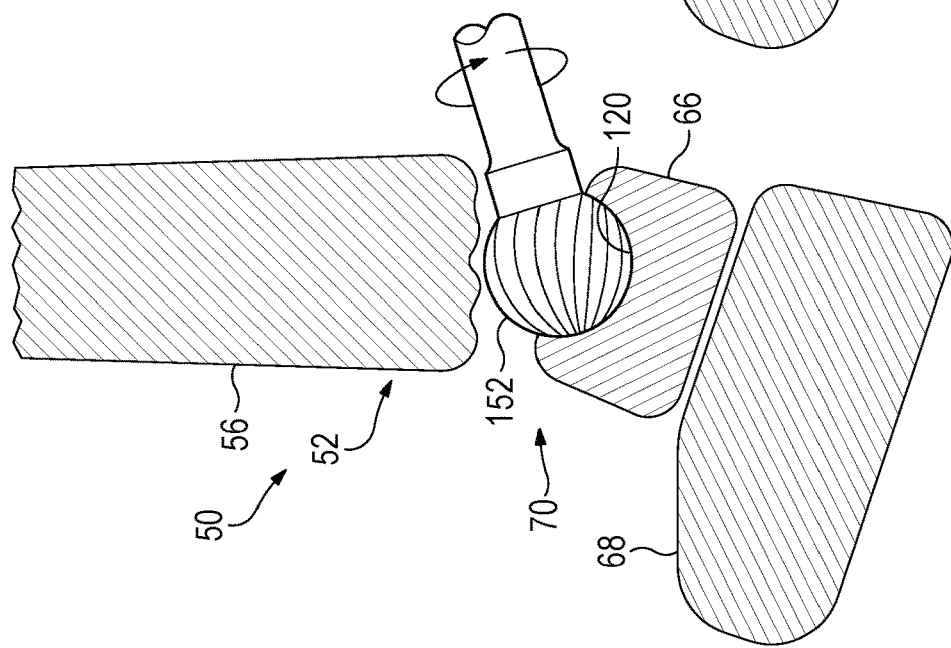

A pair of bones of ankle region 70 may be selected for abutment with spacer 92. The bones may be tibia 56 and talus 66, tibia 56 and calcaneus 68, or talus 66 and calcaneus 68 of ankle region 70. The selected bones may be prepared to be abutted with spacer 92 by creating a surface region of each bone that corresponds to a bone-contacting surface region of one of the sections of the spacer. The surface region of the bone may be a concavity that is complementary to a rounded section 100 or 102, a flat surface region for abutment with a flat end of section 100 or 102, or the like. FIGS. 14 and 15 show tibia 56 and talus 66 being prepared using a spherical reamer 152 to form concavities 118, 120. The radius of curvature of each concavity may match that of the corresponding section 100, 102 to be placed into the concavity. In other embodiments, one of the selected bones may be modified, such as by sawing, milling, or the like, to create a planar surface region.

Figure 17:
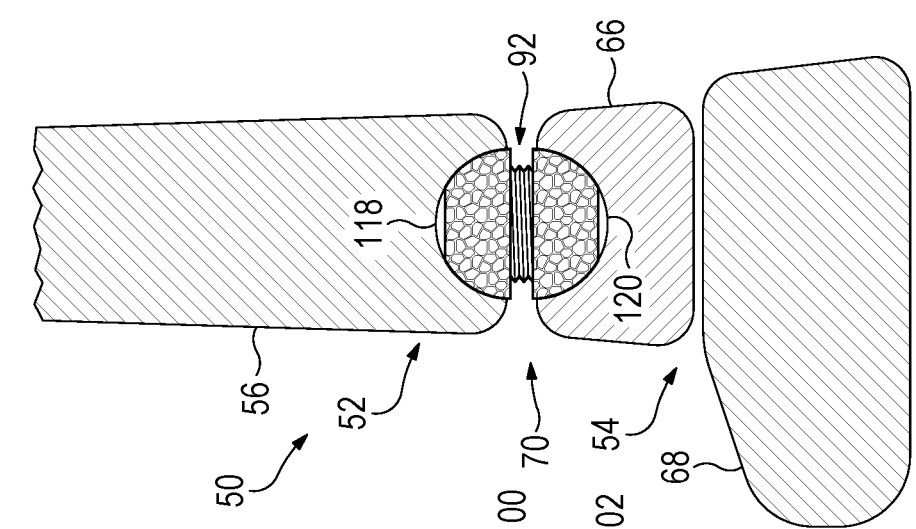
Figure 16:
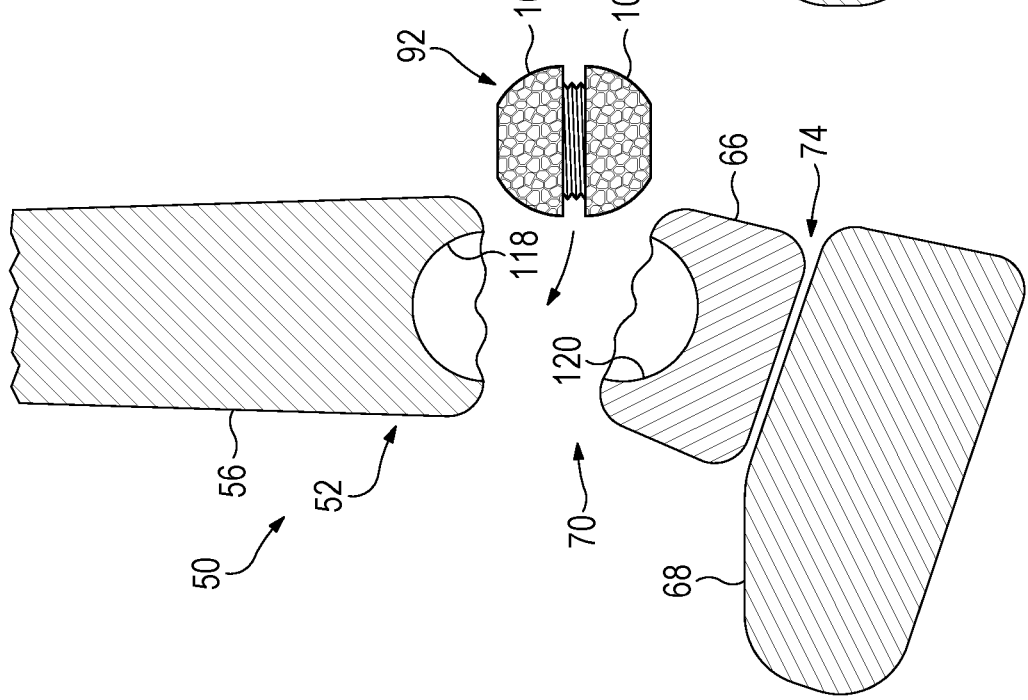

Spacer 92 may be placed between the prepared bones, such that a rounded section of spacer 92 is located in a concavity formed in one of the bones, and the other section of spacer 92 is abutted with the other bone. FIGS. 16 and 17 show spacer 92 being placed between tibia 56 and talus 66, such that sections 100, 102 are received in respective concavities 118, 120. The orientation of talus 66 (and/or another bone of ankle region 70) may be adjusted in any suitable plane(s), to change the orientation of foot 54 with respect to lower leg 52 while spacer 92 remains between the bones. The separation between the bones may be adjusted to change the length of lower limb 50 while spacer 92 remains between the bones.

Figure 18:
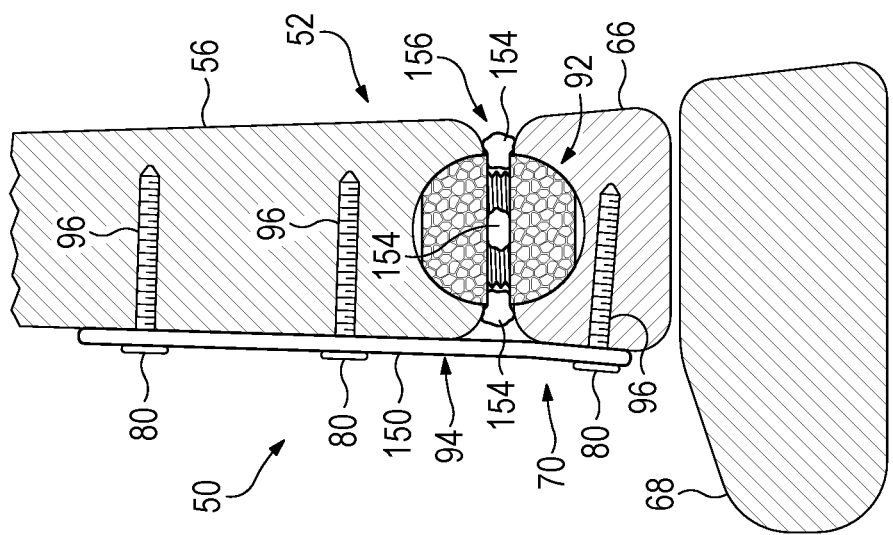

The selected bones may be fixed relative to one another using at least one fixation device, such as a nail, a bone plate, and/or one or more fasteners, among others. The fixation device(s) may avoid the spacer, or may engage the spacer (see Section III). A bone graft may be associated with the spacer and may help to fill empty space between the bones. FIG. 18 illustrates installation of bone plate 150 as fixation device 94, with the bone plate attached to tibia 56 and talus 66 using bone screws 80 as fasteners 96. A bone graft 154 has been introduced into a gap 156 between the bones

III. EXAMPLES

The following examples describe further exemplary aspects and embodiments of ankle fusion systems, expandable spacers, and methods of ankle fusion and/or fixation using the systems and spacers. These examples are intended for illustration only and should not limit the entire scope of the present disclosure.

Example 1. Spacers With Rounded and Flattened End Portions

Figure 19:
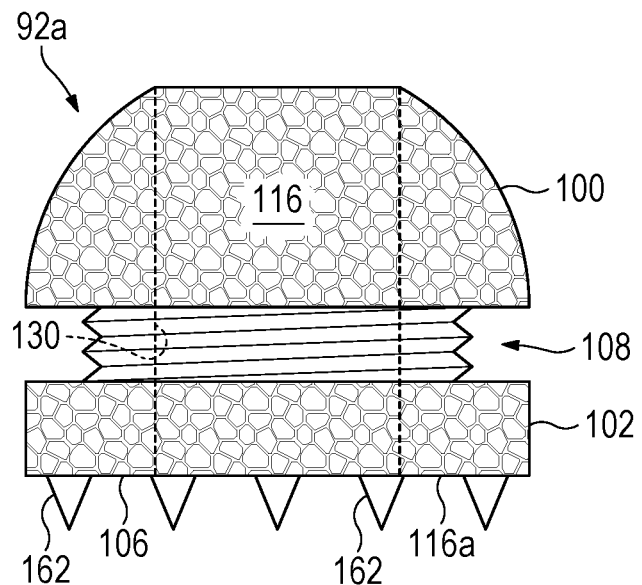
FIG. 19 is an elevational view of a second embodiment of an expandable spacer for the ankle fusion systems of the present disclosure.
Figure 20:
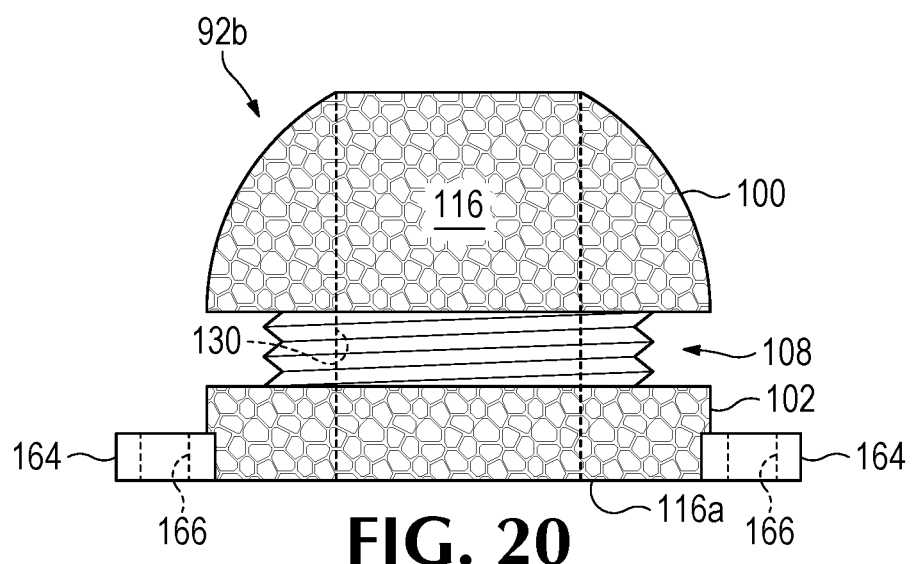
FIG. 20 is an elevational view of a third embodiment of an expandable spacer for the ankle fusion systems of the present disclosure.
Figure 21:
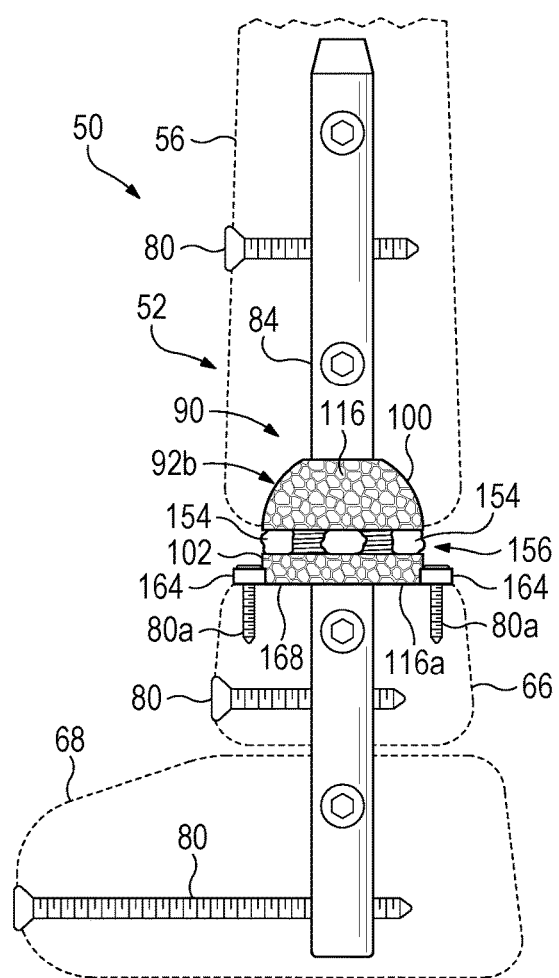
FIG. 21 is a schematic, fragmentary, lateral view of the tibia (shown fragmentary), talus, and calcaneus, each shown in dashed outline after installation of an exemplary ankle fusion system including an intramedullary nail and the expandable spacer of FIG. 20.

This example describes exemplary spacers having opposite end portions that are rounded and flattened, respectively; see FIGS. 19-21.

FIG. 19 shows another expandable spacer 92a for the ankle fusion systems of the present disclosure. Spacer 92a may have any suitable combination of elements and features described above for spacer 92, such as a rounded upper section 100, a height-adjustment mechanism 108, and/or an axial through-opening 130. However, a lower section 102 of the spacer may form a bone-contacting surface region 116a that is planar at lower end 106. Lower section 102 may have any suitable shape, such as cylindrical in the depicted embodiment. One or more prongs 162 may project from surface region 116a and may be inserted into bone when spacer 92a is abutted with a flat surface region of an adjacent bone.

FIG. 20 shows yet another expandable spacer 92b for the ankle fusion systems of the present disclosure. Spacer 92b is similar to spacer 92a except that prongs 162 may be omitted, and a plurality of ears 164 may project laterally (e.g., radially) from lower section 102. Each ear 164 defines an aperture 166 for receiving a fastener that attaches the ear to bone.

FIG. 21 shows spacer 92b establishing a gap 156 between tibia 56 and talus 66. Lower section 102 is abutted with a flat surface region 168 of talus 66 created by cutting the talus. Small screws 80a extend through ears 164 and into talus 66. Nail 84 is secured to tibia 56, talus 66, and calcaneus 68 with bone screws 80, to fix these bones relative to one another. In other embodiments, lower section 102 may be abutted with a flat surface region of tibia 56 (with spacer 92b inverted) and upper section 100 may be abutted with a concavity formed in talus 66 (or calcaneus 68).

Example 2. Spacers Lacking an Axial Through-Opening

Figure 22:
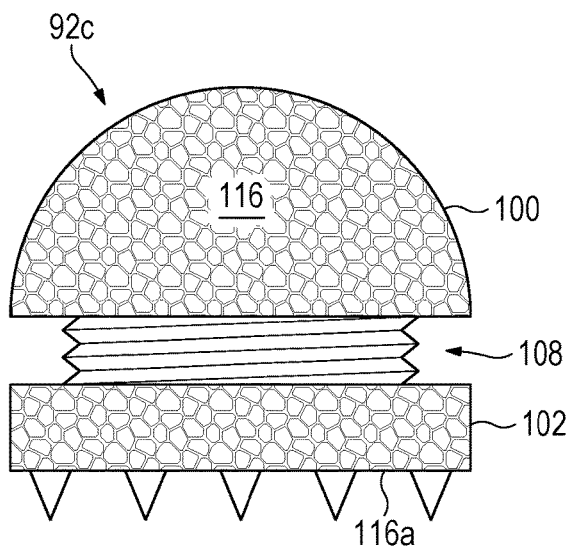
FIG. 22 is an elevational view of a fourth embodiment of an expandable spacer for the ankle fusion systems of the present disclosure.
Figure 23:
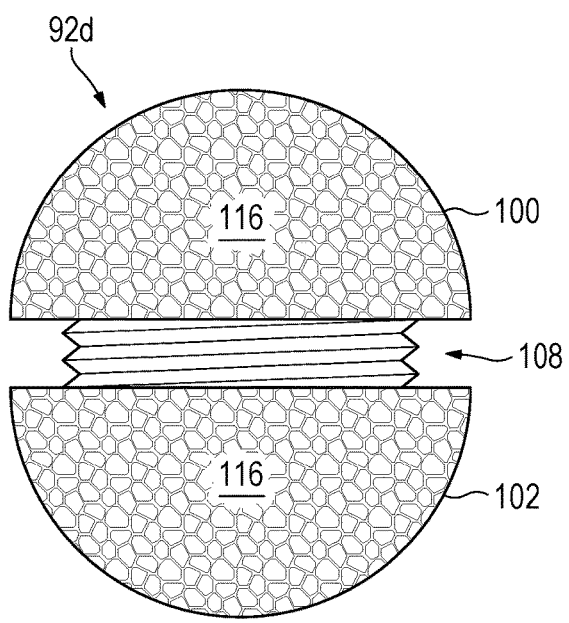
FIG. 23 is an elevational view of a fifth embodiment of an expandable spacer for the ankle fusion systems of the present disclosure.

This section describes exemplary embodiments of expandable spacers 92c, 92d lacking axial through-opening 130 (compare with spacer 92 of FIGS. 10-12); see FIGS. 22 and 23. Spacers 92c and 92d may be used with a bone plate and/or bone screws, among others.

Example 3. Spacer With Bores for Receiving Fasteners

Figures 24, 25, 26:
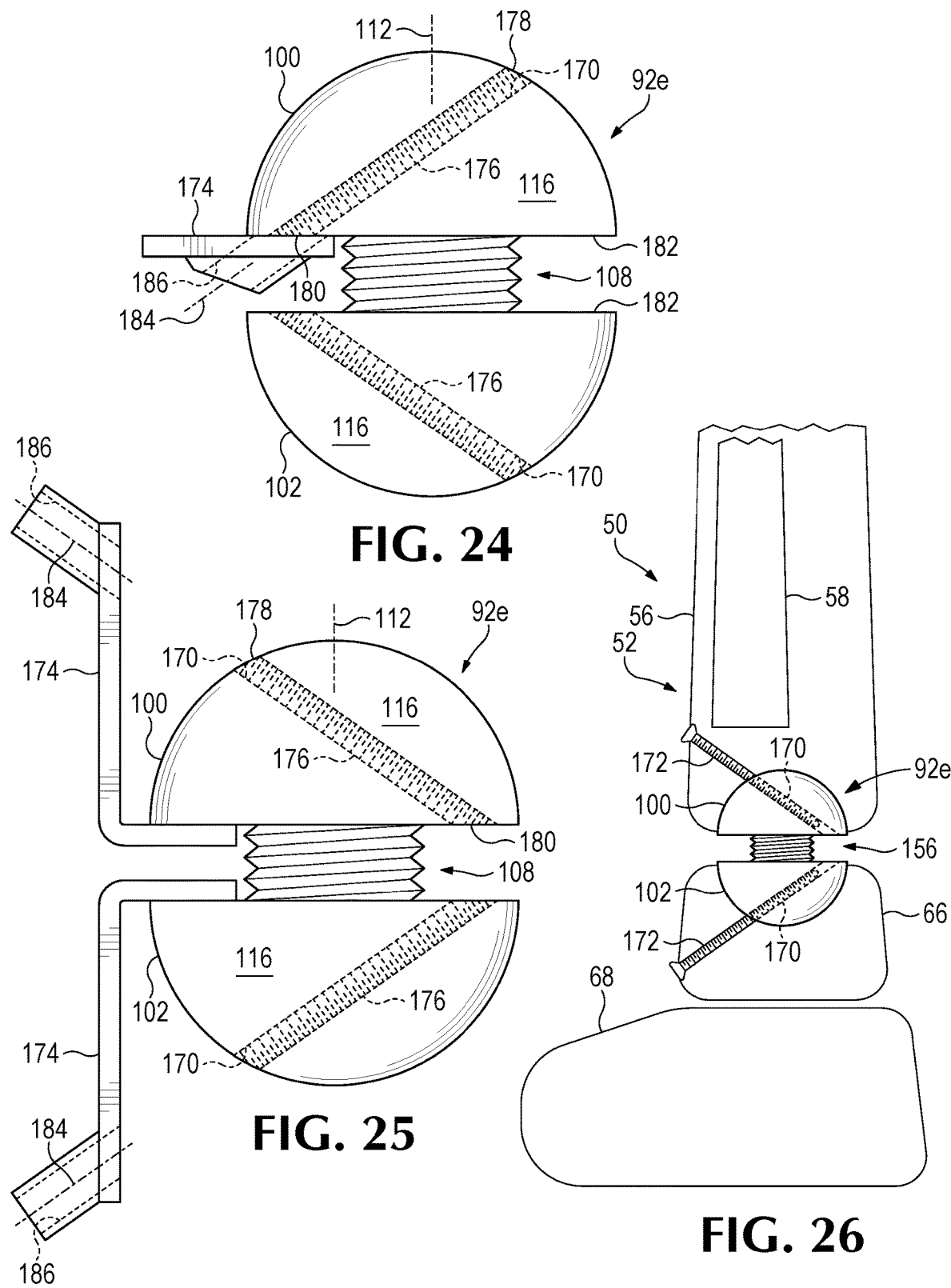
FIG. 24 is an elevational view of a sixth embodiment of an expandable spacer for the ankle fusion systems of the present disclosure, taken with an exemplary targeting guide attached to the spacer.
FIG. 25 is an elevational view of the spacer of FIG. 24 taken with two copies of a different targeting guide attached to the spacer at a different position than in FIG. 24.
FIG. 26 is a schematic, lateral view of the bones of an ankle region, taken after installation of an exemplary ankle fusion system including the spacer of FIG. 25.

This example describes an exemplary expandable spacer 92e having at least one bore 170 to receive a fastener 172, and exemplary guide devices 174 for use with the spacer; see FIGS. 24-26.

FIGS. 24 and 25 shows spacer 92e having one or more bores 170 including an internal thread 176 and formed in each section 100, 102. Each bore 170 may be oriented obliquely to axis 112 of the spacer, as shown, or may be orthogonal or parallel to axis 112. The bore may extend through one of sections 100, 102, or may be a blind bore formed by the section. One end 178 (e.g., an inlet end) of bore 170 may intersect bone-contacting surface region 116 of the corresponding section 100 or 102. An opposite end 180 (e.g., an outlet end) of bore 170 may be located at an inner end 182 of section 100 or 102.

Guide device 174 may be removably securable to at least one of sections 100, 102. Attachment may be at inner end 182 of the section, as shown here. The guide device may define a guide axis 184 that is coaxial to at least one of bores 170, such that the guide device is configured to guide a drill and/or a fastener 172 along the guide axis to or past end 178 of bore 170 formed in bone-contacting surface region 116 (or a flat bone-contacting surface region 116a (e.g., see FIG. 21)). Guide axis 184 may be coaxial with a channel 186 of the guide device.

FIG. 26 shows fasteners 172 in threaded engagement with bores 170 and securing respective sections 100, 102 of spacer 92e to tibia 56 and talus 66. Accordingly, fasteners 172, in conjunction with spacer 92e, fix tibia 56 and talus 66 relative to one another without spanning gap 156 between the bones.

Example 4. Spacers With a Collar for Adjusting Height

This example describes exemplary expandable spacers 92f, 92g having a collar 188 that is rotatable to change spacer height, and an exemplary tool 190 for rotating the collar; see FIGS. 27-30.

Figure 27:
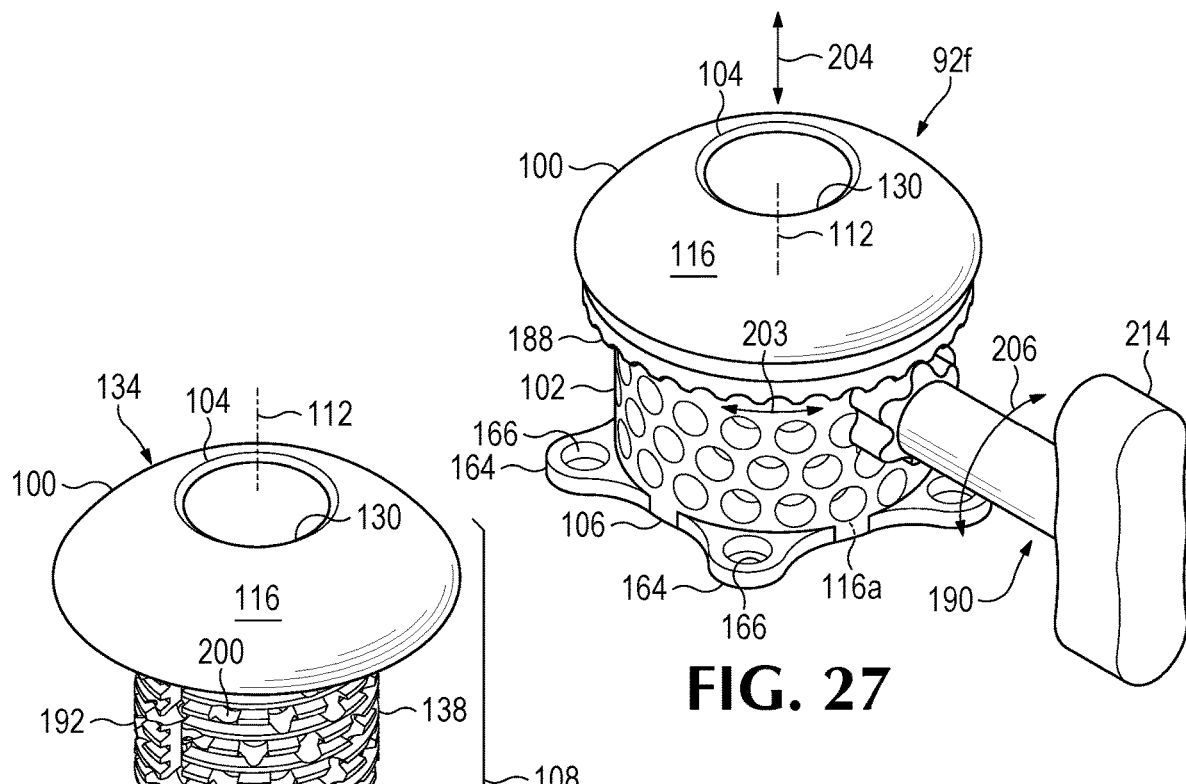
FIG. 27 is a view of a seventh embodiment of an expandable spacer for the ankle fusion systems of the present disclosure, taken with a tool removably coupled to the spacer and illustrating how the tool rotates a collar to expand the spacer.
Figure 28:
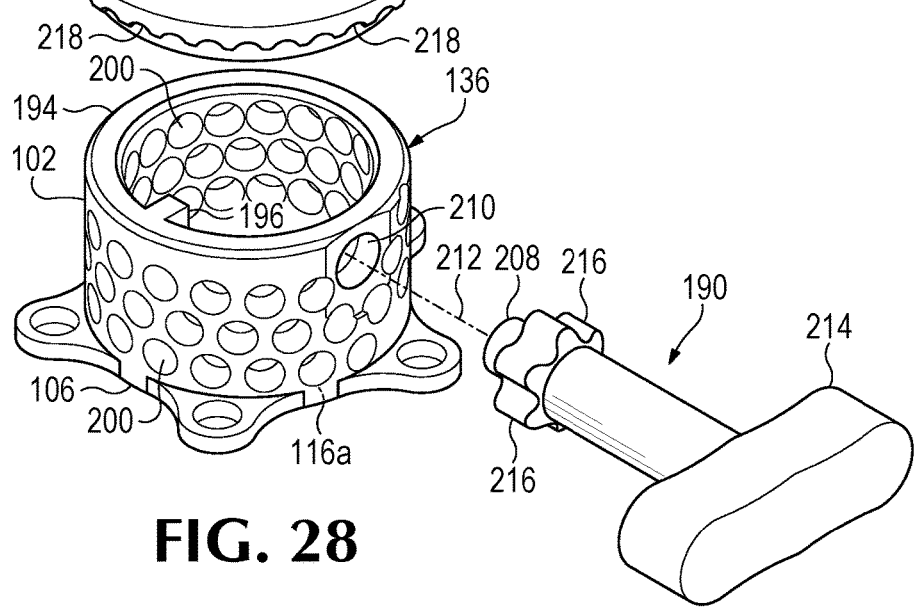
FIG. 28 is an exploded view of the spacer and tool of FIG. 27.

FIGS. 27 and 28 respectively depict spacer 92f and tool 190 fitted together and in an exploded configuration. Spacer 92f may have any suitable combination of features described elsewhere herein. The spacer has a first component 134 and a second component 136 forming respective bone-contacting surface regions 116, 116a. Surface region 116 is spherical (corresponding to a frustospherical portion of a sphere), and surface region 116a is planar. The surface regions are opposite one another, face away from one another, and extend to respective opposite ends 104, 106 of the spacer.

First and second components 134, 136 form respective inner and outer tubes 192, 194 arranged coaxially with one another. Inner tube 192 forms a shaft 138 that is attached to upper section 100 and has an external thread 140. Ears 164 project radially from outer tube 194. Rotation of tubes 192, 194 relative to one another about axis 112 is prevented by complementary axial features, such as an axial flange 196 of outer tube 194 received in an axial slot 198 defined by inner tube 192. One or both tubes 192, 194 may define through-apertures 200 or other openings to encourage bone in-growth and/or on-growth. Through-apertures 200 of either tube may be radial through-apertures and/or may form a three-dimensional arrangement of through-apertures including at least 10, 20, or 50 through-apertures or other openings.

Collar 188 has an internal thread 202 disposed in threaded engagement with external thread 140 of inner tube 192 to create a height-adjustment mechanism 108. Rotation of collar 188 drives translational movement of first component 134 along axis 112, indicated by a motion arrow at 204. This translational movement changes the length portion of inner tube 192 that is located inside outer tube 194.

Rotation of tool 190, indicated by an arrow at 206, drives translational movement 204. Tool 190 has a nose 208 for mating with a corresponding hole 210 defined by outer tube 194, to define an axis 212 of rotation for tool 190. The tool may be manipulated manually via a handle portion 214 located opposite nose 208. Radial protrusions 216 are formed on the shaft of tool 190. Collar 188 has a circular series of teeth 218 for engagement with radial protrusions 216. Rotation of tool 190 about axis 212 successively advances individual teeth of the series of teeth past the tool.

Figure 29:
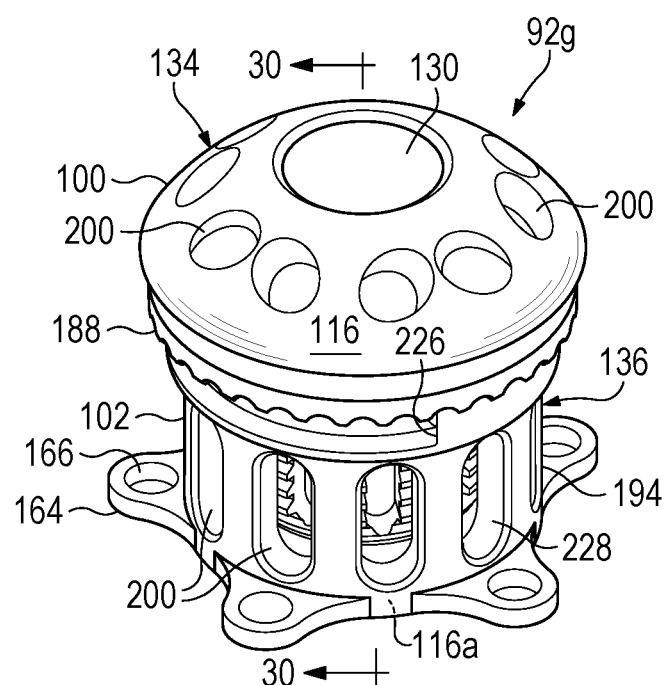
FIG. 29 is a view of an eighth embodiment of an expandable spacer for the ankle fusion systems of the present disclosure.
Figure 30:
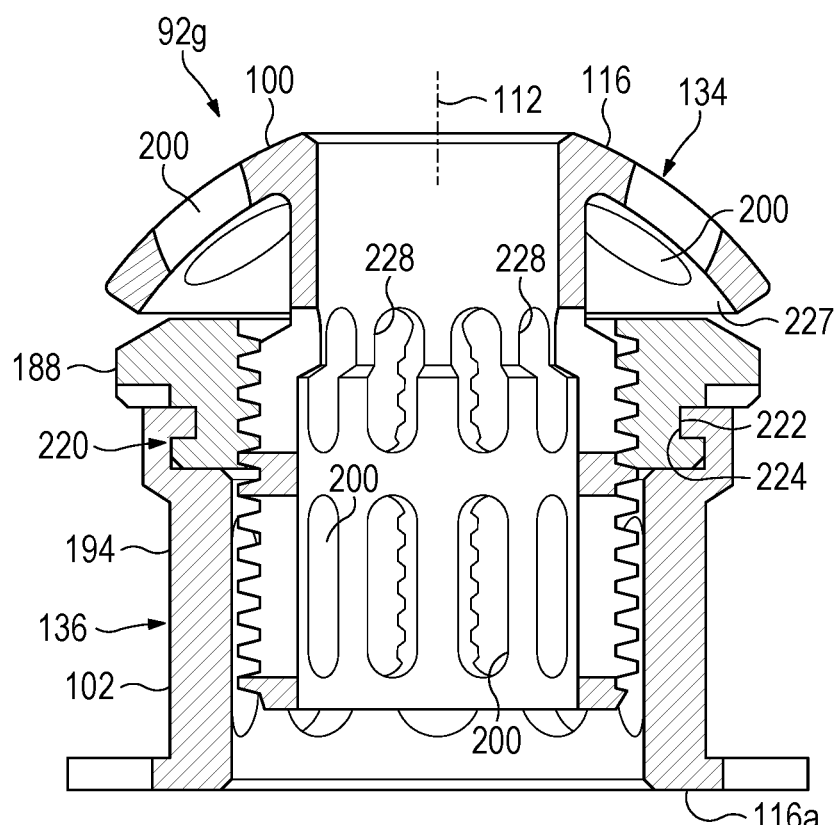
FIG. 30 is a sectional view of the spacer of FIG. 29, taken generally along line 30-30 of FIG. 29.

FIGS. 29 and 30 show another spacer 92g, which has a generally similar overall structure to 92f. In spacer 92g, collar 188 has a rotatable connection 220 to outer tube 194 of second component 136, which permits rotation of the collar and tube relative to one another about axis 112, while preventing axial separation of the collar and outer tube from one another. The rotatable connection may be formed, at least in part, by complementary mating features including at least one annular groove 222 of one of the collar and outer tube fitted together with a flange 224 of the other of the collar and outer tube. The collar and outer tube may be mated with one another, during manufacture or peri-operatively, to engage the mating features with one another. This mating may be performed along a mating axis that is orthogonal to axis 112 of spacer 92g. Flange 224 may extend only partway around axis 112 to create a mouth 226 through which a lower portion of the collar can travel for engagement of groove 222 with flange 224. The mouth can be sized such that the collar travels through the mouth only with application of substantial force, and thus is not removable through mouth 226 during normal handling or after installation in a subject.

Spacer 92g defines through-apertures 200 in upper section 100, inner tube 192, and outer tube 194 to encourage bone in-growth. Upper section 100 may define through-apertures 200 that extend from bone-contacting surface region 116 to an inner surface region 227. Any of the through-apertures can be slots 228, which may be elongated axially in tubes 192, 194.

Example 5. Selected Embodiments

This example describes selected embodiments of the spacers, ankle fusion systems, and ankle fusion methods of the present disclosure as a series of indexed paragraphs.

Paragraph A1. An implantable device for separating a first bone and a second bone of an ankle region, the device comprising: an expandable spacer including a first bone-contacting surface region configured to be abutted with the first bone and a second bone-contacting surface region configured to be abutted with the second bone to produce a separation of the first bone and the second bone from one another, the first and second bone-contacting surface regions facing away from one another, a distance between the first and second bone-contacting surface regions being adjustable to change the separation of the first and second bones, the first bone-contacting surface region corresponding to a portion of a sphere and being configured to be disposed at least partially in a concavity formed surgically in the first bone.

Paragraph A2. The device of paragraph A1, wherein the spacer includes a threaded mechanism for adjusting the distance between the first and second bone-contacting surface regions.

Paragraph A3. The device of paragraph A2, wherein the threaded mechanism includes a threaded member that is rotatable with respect to the first and second bone-contacting surface regions to adjust the distance between such surface regions.

Paragraph A4. The device of paragraph A3, wherein the threaded member includes an internally-threaded collar.

Paragraph A5. The device of paragraph A4, wherein the spacer includes a first component and a second component respectively providing the first and second bone-contacting surface regions, and wherein one of the first and second components has an externally-threaded shaft disposed in threaded engagement with the collar.

Paragraph A6. A system comprising the device of paragraph A4 or paragraph A5, wherein the collar has a series of teeth arranged on a circle, further comprising a tool configured to successively advance individual teeth of the series of teeth past the tool as the tool is rotated.

Paragraph A7. An ankle fusion system comprising the device of any of paragraphs A1 to A5 and a fixation device configured to be secured to each of the first and second bones, to fix the first and second bones relative to one another while the spacer is located between the bones.

Paragraph A8. The system of paragraph A7, wherein the fixation device includes a nail, a plate, or a fastener.

Paragraph A9. The device of any of paragraphs A1 to A5, wherein the first bone-contacting surface region corresponds to no more than about a hemisphere.

Paragraph A10. The device of any of paragraphs A1 to A5 and A9, wherein the first bone-contacting surface region corresponds to a frustum of a sphere.

Paragraph A11. The device of any of paragraphs A1 to A5, A9, and A10, wherein the spacer defines an axial opening that extends through the device along a central axis.

Paragraph A12. The device of paragraph A11, wherein the distance is adjustable parallel to the central axis, and wherein each of the bone-contacting surface regions is centered on the central axis.

Paragraph A13. An ankle fusion system comprising the device of paragraph A11 or A12 and a nail configured to extend through the spacer via the axial opening.

Paragraph A14. The device of any of paragraphs A1 to A5 and A9 to A12, wherein the first bone-contacting surface region is configured to encourage bone in-growth and/or bone on-growth.

Paragraph A15. The device of paragraph A14, wherein the first bone-contacting surface region is created by an open cellular structure.

Paragraph A16. The device of paragraph A15, wherein the open cellular structure includes a mesh, a lattice, or a foam.

Paragraph A17. The device of any of paragraphs A14 to A16, wherein the spacer includes a first section that forms the first bone-contacting surface region and an inner surface region, wherein the first section defines a plurality of apertures and/or a plurality of pores that extend from the first bone-contacting surface region to the inner surface region.

Paragraph A18. The device of any of paragraphs A1 to A5, A9 to A12, and A14 to A17, wherein the second bone-contacting surface region is planar.

Paragraph A19. The device of paragraph A18, wherein the distance between the first and second bone-contacting surface regions is adjustable along an axis, and wherein the second bone-contacting surface region is orthogonal to the axis.

Paragraph A20. The device of any of paragraphs A1 to A5, A9 to A12, and A14 to A19, wherein the spacer includes a first component providing the first bone-contacting surface region and a second component providing the second bone-contacting surface region, wherein the second component includes a tube and a plurality of ears projecting from the tube, and wherein each ear defines an aperture configured to receive a fastener that secures the ear to the second bone.

Paragraph A21. The device of paragraph A20, wherein each ear is flush with the second bone-contacting surface region.

Paragraph A22. The device of any of paragraphs A1 to A5, A9 to A12, and A14 to A21, wherein the distance between the first and second bone-contacting surface regions is adjustable without changing the shape of either bone-contacting surface region.

Paragraph A23. The device of any of paragraphs A1 to A5, A9 to A12, and A14 to A22, wherein the first bone-contacting surface region includes depressions and/or projections that encourage bone on-growth.

Paragraph A24. The device of any of paragraphs A1 to A5, A9 to A12, and A14 to A23, wherein the second bone-contacting surface region corresponds to a portion of a sphere.

Paragraph A25. The device of paragraph A24, wherein the second bone-contacting surface region corresponds to no more than about a hemisphere.

Paragraph A26. The device of paragraph A24 or A25, wherein the second bone-contacting surface region corresponds to a frustum of a sphere.

Paragraph A27. The device of any of paragraphs A1 to A5, A9 to A12, and A14 to A26, wherein the spacer defines a bore intersecting the first bone-contacting surface region and having an internal thread.

Paragraph A28. An ankle fusion system comprising the device of paragraph A27 and a fastener configured to be disposed in threaded engagement with the bore.

Paragraph A29. The system of paragraph A28, further comprising a guide device configured to be connected to the spacer and defining a guide axis that is coaxial with the bore.

Paragraph A30. The system of paragraph A29, wherein the guide device includes a tube that defines the guide axis.

Paragraph A31. The device of any of paragraphs A1 to A5, A9 to A12, and A14 to A27, wherein one of the first and second bones is a tibia, and wherein the other of the first and second bones is a talus or a calcaneus.

Paragraph A32. The device of any of paragraphs A1 to A5, A9 to A12, A14 to A28, and A31, wherein the first bone-contacting surface region is created by additive manufacturing.

Paragraph A33. The device of any of paragraphs A1 to A5, A9 to A12, A14 to A28, A31, and A32, wherein the first bone-contacting surface region has surface features produced by local, random variations in elevation.

Paragraph A34. The device of any of paragraphs A1 to A5, A9 to A12, A14 to A28, and A31-A33, wherein the first and second bone-contacting surface regions are configured to move translationally relative to one another to change the distance between such surface regions.

Paragraph B1. A method of fusing a first bone and a second bone of an ankle region, the method comprising in any order: (i) forming a concavity in the first bone; (ii) disposing an expandable spacer between the first and second bones, such that a first bone-contacting surface region of the spacer is abutted with the first bone in the concavity and such that a second bone-contacting surface region of the spacer is abutted with the second bone to produce a separation of the first bone and the second bone from one another, wherein a distance between the first and second bone-contacting surface regions is adjustable to change the separation of the first and second bones; and (iii) fixing the first and second bones relative to one another.

Paragraph B2. The method of paragraph B1, wherein the step of forming a concavity includes a step of removing part of the first bone using a spherical reamer.

Paragraph B3. The method of paragraph B1 or B2, wherein one of the first and second bones is a tibia, and wherein the other of the first and second bones is a talus or a calcaneus.

Paragraph B4. The method of any of paragraphs B1 to B3, wherein the second bone-contacting surface region corresponds to a portion of a sphere, further comprising a step of forming a concavity in the second bone that is sized to receive the second bone-contacting surface region.

Paragraph B5. The method of any of paragraphs B1 to B3, further comprising a step of forming a flat surface region on the second bone, wherein the step of disposing includes a step of abutting the second bone-contacting surface region and the flat surface region with one another.

Paragraph B6. The method of any of paragraphs B1 to B5, further comprising a step of adjusting an orientation of the first and second bones relative to one another while the spacer remains between the first and second bones.

Paragraph B7. The method of any of paragraphs B1 to B6, wherein the step of fixing includes a step of securing a nail, a plate, or a fastener to each of the first and second bones.

Paragraph B8. The method of paragraph B7, wherein the step of securing includes a step of securing a nail to each of the first and second bones, and wherein the nail extends through the spacer.

Paragraph B9. The method of paragraph B8, wherein the step of securing includes a step of securing a plate to each of the first and second bones using a plurality of fasteners.

Paragraph B10. The method of paragraph B1, wherein the step of fixing includes a step of attaching a fastener directly to the spacer.

Paragraph B11. The method of paragraph B10, wherein the step of attaching a fastener includes a step of disposing a fastener in threaded engagement with a bore defined by the spacer.

Paragraph B12. The method of any of paragraphs B1 to B11, further comprising a step of adjusting the distance between the first and second bone-contacting surface regions, to change the separation between the first and second bones.

Paragraph B13. The method of paragraph B12, wherein the method is performed on the ankle region of a subject, and wherein the step of adjusting the distance reduces a difference in length of the lower limbs of the subject.

Paragraph B14. The method of paragraph B12 or B13, wherein the step of adjusting the distance includes a step of rotating a threaded member of the spacer relative to the first and second bone-contacting surface regions.

Paragraph B15. The method of any of paragraphs B1 to B14, further comprising a step of disposing a bone graft in and/or on the spacer.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

I claim:

1. A system comprising:
an implantable device for separating a first bone and a second bone of an ankle region, the implantable device comprising an expandable spacer including a first bone-contacting surface region configured to be abutted with the first bone and a second bone-contacting surface region configured to be abutted with the second bone to produce a separation of the first bone and the second bone from one another, the first and second bone-contacting surface regions facing away from one another, a distance between the first and second bone-contacting surface regions being adjustable to change the separation of the first and second bones, the first bone-contacting surface region corresponding to a portion of a sphere and being configured to be disposed at least partially in a concavity formed surgically in the first bone, wherein the expandable spacer includes a threaded member that is rotatable with respect to the first and second bone-contacting surface regions to adjust the distance between such surface regions, and wherein the threaded member has a series of teeth arranged on a circle; and
a tool configured to successively advance individual teeth of the series of teeth past the tool as the tool is rotated.

2. The system of claim 1, further comprising a fixation device configured to be secured to each of the first and second bones, to fix the first and second bones relative to one another while the expandable spacer is located between the bones.

3. The system of claim 2, wherein the fixation device includes a nail, a plate, or a fastener.

4. The system of claim 1, wherein the first bone-contacting surface region corresponds to no more than about a hemisphere.

5. The system of claim 1, wherein the spacer defines an axial opening that extends through the implantable device along a central axis.

6. The system of claim 1, wherein the first bone-contacting surface region is configured to encourage bone in-growth and/or bone on-growth.

7. The system device of claim 1, wherein the second bone-contacting surface region is planar.

8. The system of claim 1, wherein the distance between the first and second bone-contacting surface regions is adjustable without changing the shape of either bone-contacting surface region.

9. The system of claim 1, wherein the expandable spacer defines a bore intersecting the first bone-contacting surface region and having an internal thread.

10. The system of claim 9, further comprising a guide device configured to be connected to the expandable spacer and defining a guide axis that is coaxial with the bore.

11. A method of fusing a first bone and a second bone of an ankle region, the method comprising:
selecting the implantable device of claim 1;
forming a concavity in the first bone;
disposing the expandable spacer between the first and second bones, such that the first bone-contacting surface region of the expandable spacer is abutted with the first bone in the concavity and such that the second bone-contacting surface region of the spacer is abutted with the second bone to produce a separation of the first bone and the second bone from one another; and
fixing the first and second bones relative to one another.

12. The method of claim 11, wherein one of the first and second bones is a tibia, and wherein the other of the first and second bones is a talus or a calcaneus.

13. The method of claim 11, wherein the step of fixing includes a step of securing a nail, a plate, or a fastener to each of the first and second bones.

14. The method of claim 11, wherein the step of fixing includes a step of attaching a fastener directly to the expandable spacer, and wherein the step of attaching a fastener includes a step of disposing the fastener in threaded engagement with a bore defined by the expandable spacer.

15. A system for separating a first bone and a second bone of an ankle region, the system comprising:
an expandable spacer including a first bone-contacting surface region configured to be abutted with the first bone and a second bone-contacting surface region configured to be abutted with the second bone to produce a separation of the first bone and the second bone from one another, the first and second bone-contacting surface regions facing away from one another, a distance between the first and second bone-contacting surface regions being adjustable to change the separation of the first and second bones, the first bone-contacting surface region corresponding to a portion of a sphere and being configured to be disposed at least partially in a concavity formed surgically in the first bone, wherein the expandable spacer defines a bore intersecting the first bone-contacting surface region and having an internal thread; and
a guide device configured to be connected to the expandable spacer and defining a guide axis that is coaxial with the bore.

16. The system of claim 15, further comprising a fixation device configured to be secured to each of the first and second bones, to fix the first and second bones relative to one another while the expandable spacer is located between the bones.

17. The system of claim 16, wherein the fixation device includes a nail, a plate, or a fastener.

18. The system of claim 15, wherein the first bone-contacting surface region corresponds to no more than about a hemisphere.

19. The system of claim 15, wherein the expandable spacer defines an axial opening that extends through the implantable device along a central axis.

20. The system of claim 15, wherein the first bone-contacting surface region is configured to encourage bone in-growth and/or bone on-growth.

21. The system of claim 15, wherein the second bone-contacting surface region is planar.

22. The system of claim 15, wherein the distance between the first and second bone-contacting surface regions is adjustable without changing the shape of either bone-contacting surface region.

* * * * *